United States Patent [19]

Smith et al.

[11] Patent Number: 5,321,049

[45] Date of Patent: Jun. 14, 1994

[54] AGRICULTURAL COMPOSITIONS CONTAINING LATEXES

[75] Inventors: Geoffrey W. Smith, Faringdon; Patrick J. Mulqueen, Abingdon; Eric S. Paterson, Wantage; John Cuffe, Heacham, all of Great Britain

[73] Assignee: DowElanco, Indianapolis, Ind.

[21] Appl. No.: 469,426

[22] PCT Filed: Oct. 14, 1988

[86] PCT No.: PCT/GB88/00862

§ 371 Date: Apr. 5, 1990

§ 102(e) Date: Apr. 5, 1990

[87] PCT Pub. No.: WO89/03175

PCT Pub. Date: Apr. 20, 1989

[30] Foreign Application Priority Data

Oct. 14, 1987 [GB] United Kingdom ............. 3724133
Oct. 14, 1987 [GB] United Kingdom ............. 8724132
Jul. 27, 1988 [GB] United Kingdom ............. 8817930.4

[51] Int. Cl.⁵ .......................................... A01N 25/10
[52] U.S. Cl. ............................. 514/772.6; 514/772.4
[58] Field of Search ................... 424/405, 78, 409; 514/772.6, 772.4

[56] References Cited

U.S. PATENT DOCUMENTS 3,400,093  9/1968  Feinberg ........................ 260/29.6
4,818,536  4/1989  Meyers et al. ..................... 424/409

FOREIGN PATENT DOCUMENTS 0708798   1/1968  Belgium .
3304457  10/1983  Fed. Rep. of Germany .
58-072501 4/1983  Japan .
0658222   5/1949  United Kingdom .
1367137   8/1971  United Kingdom .
2072506   2/1981  United Kingdom .
2138291  10/1984  United Kingdom .

OTHER PUBLICATIONS

Basic Abstracts Journal, Section C, week K23, Aug. 3, 1983, No. 55173, Derwent Publications.

Primary Examiner—Thurman K. Page
Assistant Examiner—N. Levy
Attorney, Agent, or Firm—S. Preston Jones

[57] ABSTRACT

A stabilized water dilutable pesticidal composition prepared by forming a solution of a pesticidal substance in a water-immiscible solvent, and combining the solution with an emulsifier and a polymer latex to form a dispersion in water of particles comprising the pesticidal substance wherein the pesticidal substance and the water-immiscible solvent together comprise at least 10 percent by weight of the composition.

5 Claims, No Drawings

AGRICULTURAL COMPOSITIONS CONTAINING LATEXES

This invention relates to agricultural compositions, and in particular to herbicidal, fungicidal and insecticidal compositions (hereinafter referred to as pesticidal compositions) for both pre-emergence and post-emergence application.

It is generally desired of such pesticidal compositions that they should be easy to handle, and easy to apply in any desired concentration. For this reason, herbicidal compositions are generally supplied in the form of wettable powders, emulsifiable concentrates and the like. In the formulation of emulsifiable concentrates, it is generally necessary to incorporate substantial quantities of organic solvents, and this can result in substantial problems of dermal toxicity and flammability. Furthermore, because of the presence of organic solvents, it is not possible, for many emulsifiable concentrate compositions, to utilize containers of conventional plastics materials, such as high density polyethylene (HDPE). Instead, such concentrates have to be contained within specially designed containers, which are resistant to the solvents used. In addition, the incorporation of high levels of organic solvents in emulsifiable concentrates gives rise to problems of phytotoxicity to crops when the pesticidal substances are utilized.

EP-A-0080516 (Dow), discloses insecticidal compositions, in which the active substance is incorporated within particles of a latex, and that thereby water-borne dispersions may be prepared. These prior art disclosures are however restricted to the use of specific insecticides, chlorpyrifos and chlorpyrifos-methyl, and the disclosure indicates that it is essential that the pesticide utilized is either a liquid or a low-melting solid at ambient temperatures, so that it can be solubilized into the polymer at temperatures less than 100° C. as a liquid.

Furthermore, although the method disclosed in EP 0080516 enables the preparation of latex-containing compositions of chlorpyrifos, its method requires that the active substance should be heated to 60° C. for 2 hours. This is both inconvenient to carry out industrially, and can give rise to thermal degradation of the chlorpyrifos.

In addition the method is very unsatisfactory with pesticides which have a somewhat higher melting point.

GB-A-2072506 (Desowag-Bayer) is concerned with a film-forming wood preservative concentrate substantially free of inorganic salts or pigments. The compositions disclosed therein comprise an insecticide or fungicide, a water insoluble solvent, and a water-dilutable aqueous plastics dispersion which may be a polymer or copolymer of a vinyl ester, an acrylic acid ester, or a methacrylic acid ester. The compositions also comprise from 0 to 2% of an emulsifier. Although the compositions are somewhat dilutable in water (up to 1:4), the compositions are not in the nature of suspension concentrates, i.e. ones which are essentially infinitely dilutable (particularly diluable up to at least 50:1) in water. This is not surprising when it is considered that the essential characteristic of the compositions of the reference is that they contain drying oils and/or an alkyd resin. They are thus in the nature of paints, for application to timber and the like and the purpose of the latex in the composition is to act as a film-former.

It is inconsistent with the latex acting as film-former that high levels of surfactant should be present, and in particular that a sufficient amount of surfactant should be present to enable the compositions to be essentially infinitely dilutable with water). It is well known that the presence of surfactants will interfere with the film forming properties of latex dispersions such as are described in GB-A-2072506, such that incomplete and non-adhesive deposits will be produced, and not the continuous adherent films which the Patentees seek to produce.

It is also to be noted that none of the compositions specifically disclosed in the reference actually contain any added surfactant. Many commercially available latex compositions contain levels of surfactant of 0.5 to 5% as purchased. Dilution of such latex compositions to the levels indicated in the Examples in the reference would result in an overall surfactant level in the composition of 2% at most. It appears therefore that the Patentee was not really contemplating added surfactant when he talked about surfactant levels of up to 2%, but only that which would be inevitably present because of the latex used.

For all these reasons this reference would not readily offer itself to the expert as a starting point, when attempting to make infinitely dilutable compositions, because the fields of technology are essentially different.

GB-A-658222 (B. F. Goodrich) discloses pesticidal composition containing a latex of PVC or the like, to assist the active material to stick to the intended substrate. This patent is not however concerned with the preparation of stabilized concentrate solutions.

Similarly, U.S. Pat. No. 3,400,093 (Feinberg) discloses insecticide-containing compositions including polymers and polymer latexes. The latexes are present in these compositions to improve their coating properties and the compositions are like those of GB-A-2072506 and GB-A-658222, not essentially infinitely water-dilutable concentrates.

DE-A-3004457 (Toagosei Chem Ind (sic)) is concerned with the dispersion of solid pesticidal particles within a latex, and does not relate to the preparation of dilutable concentrates, by the dissolution of a pesticidal substance to form an emulsion, subsequently stabilized by a latex.

JP-A-8072-501 (Toa Gosei Chem Ind) is concerned with the preparation of what are effectively solutions of high molecular weight polymers, including pesticidal substances, which are obtained by the neutralization of an acid dispersion of a copolymer with an alkali. This reference is not concerned with the stabilization of pesticide-containing emulsions, using polymer latexes.

GB-A-2138291 (Tzang) is also concerned with the coating compositions in the nature of paints, containing insecticidally active ingredients. These compositions contain polymer latexes, but the compositions do not contain the amounts of surfactant which would be necessary to render them infinitely dilutable in water.

BE-A-708798 is similar in some ways in its disclosure to EP 0080516, in that it is concerned with insecticidal compositions, in which the insecticidal material can be directly imbibed into the particles of a latex for application purposes It is thus not a practical proposition for active materials which are neither water- soluble nor liquid.

GB 1367137 (PVO International) is concerned with insecticidal compositions for mothproofing of wool. The aim of the invention is to improve the persistence of insecticides in a treated fabric, by holding the insecticidal material in place on the woollen substrate, using a polymer, which has been polymerized in situ. This is achieved by applying the insecticidal material as a composition including a polymerizable resin. Such resins are, in some embodiments, used in the form of a latex. It is essential that the resin present in the composition should be further polymerizable, so that the in situ polymerisation can be carried out, and the term polymerizable resin is defined to include monomers, and pre-polymers. There is no suggestion in this reference of the use of a fully polymerized polymer latex, i.e. one which cannot be further polymerised in situ to provide a polymer to assist in the binding of the insecticidal material to a substrate. Furthermore, there is no suggestion of any stabilization of the emulsion composition by the prepolymer latexes employed in the reference. It should be noted that this reference requires specifically that the active material employed, should have very low water solubility, specifically a water solubility of not more than 500 parts per billion by weight (ppb) (see page 4, lines 3-24, and page 14, line 95 to page 15 line 10). Lastly, it should be noted that, because the prepolymer latex in the reference is employed to bind the active material to the wool substrate, the amounts of latex employed, in relation to the oil phase in the emulsion, are relatively high. In particular, all of the examples in the reference which use a latex show a ratio of resin (i.e. latex solids) to oil phase (generally, active ingredients plus solvents) of at least 1:1.

We have discovered, that an aqueous latex can be used to substantially stabilize an emulsion formed by dissolving in an appropriate water-immiscible solvent and subsequently forming an oil-in-water emulsion, of a pesticidal substance which is not freely water miscible. The method can be used to form a stable dispersion in water of particles comprising the pesticidal substance, in a manner which is very convenient to carry out on an industrial scale and without the need for heating the pesticidal substance, even for pesticidal substances with relatively high melting points. The aqueous dispersions produced are stabilized by the presence of the latex material, such that they are essentially infinitely dilutable with water (i.e. they may diluted with water at least to a dilution of 50:1 by weight).

This emulsion stabilizing effect of polymer latexes is nowhere disclosed in any of the above references although some of the compositions disclosed in GB-A-1367137 are latex-containing emulsions. However, the stabilization effect which we have discovered can be employed not only with the highly insoluble actives which are the only ones suitable for the process of GB-A-1367137, but also with actives which, although not freely water-soluble, nevertheless have a water solubility in excess of 500 p.p.b. The stabilization effect is also of particular value when the latex employed is a latex not of a prepolymer, but of a polymer which is not further polymerizable (i.e. one which is not a prepolymer intended to be further crosslinked after application, such as those utilized in GB-A-1367137, but is essentially a finished polymer).

In accordance with a first aspect of the present invention, there is therefore provided a stabilized water dilutable pesticidal composition for agricultural use which has been prepared by forming a solution in a water-immiscible solvent of a pesticidal substance which is not freely soluble in water but has a water solubility of at least 500 parts per billion by weight, and combining the solution with an emulsifier and an aqueous polymer latex to form a dispersion in water of particles comprising the pesticidal substance, wherein the pesticidal substance and the water immiscible solvent together comprise at least 10% by weight of the composition, and wherein the amount and nature of the emulsifier is such that the composition is dilutable in water, at least to a dilution of 50:1 by weight.

The invention also provides a stabilized water dilutable pesticidal composition for agricultural use which has been prepared by forming a solution of a pesticidal substance in a water-immiscible solvent, and combining the solution with an emulsifier and an aqueous latex of a polymer which is not further polymerizable to form a dispersion in water of particles comprising the pesticidal substance, wherein the pesticidal substance and the water immiscible solvent together comprise at least 10% by weight of the composition, and wherein the amount and nature of the emulsifier is such that the composition is dilutable in water, at least to a dilution of 50:1 by weight.

The term "particles" as used herein is not meant to carry with it any implication as to the physical state (i.e. liquid or solid) of the dispersed phase, and specifically is intended to include within its scope droplets comprising the pesticidal substance. It should also be understood that the term "water immiscible" as used herein is not intended to signify that the solvent is totally water-immiscible but only that the solvent is not freely miscible with water.

The term "latex" as used herein is intended to include any polymeric product produced as an aqueous suspension emulsion polymerization process and includes within its scope both synthetic latexes and natural latexes.

The term "water dilutable" as used herein is intended to mean that the pesticidal composition may effectively be diluted in water to any desired dilution e.g. to a dilution of at least 50:1 (water:composition) by weight, typical 500:1, without flocculation or coagulation.

The compositions in accordance with the invention contain an amount of an appropriate emulsifier (i.e. a surfactant), such that the resulting composition is effectively dilutable in water at least to a dilution of 50:1 by weight, preferably greater. The composition preferably comprises more than 2% by weight emulsifier, and at least 0.5% by weight of the composition is preferably added emulsifier (i.e. emulsifier which is not present in the latex composition as supplied by the manufacturer).

In preferred examples of the composition of the invention the water dilutability of the composition is retained, even in the presence of electrolytes, such as ionic fertilizers or pesticides.

Preferred latexes comprise polymers and copolymers of styrene, alkyl styrenes, isoprene, butadiene, acrylonitrile lower alkyl acrylates, vinyl chloride, vinylidene chloride, vinyl esters of lower carboxylic acids and alpha, beta-ethylenically unsaturated carboxylic acids, including polymers containing three or more different monomer species copolymerized therein, the size of the polymeric particles being in the range of from 0.03 to 20 microns, preferably from 0.1 to 10 microns. Small amounts for example 0 to 10% of bifunctional monomers may be employed to crosslink the polymers if desired.

Specifically, it has been discovered that particularly good results are obtained when the initial droplet size of the emulsion formed is from 1 to 100 microns, wherein the latex employed has a particle size of from 0.03 to 20 microns, and wherein the resulting dispersion formed has a particle size which lies between that of the initially-formed emulsion particles, and that of the latex particles. This can be determined by examining optically the average particle size of the dispersion formed, and noting the change in particle size.

In general, it is found that an emulsion having a relatively large particle size (1 to 100 microns) is formed initially, but that the droplet size decreases with time. It is believed the latex combines with the emulsion droplets to produce a dispersion having a substantial number of particles with an intermediate particle size, for example in the range of 0.03 to 20 microns, preferably from 0.1 to 10 microns, more preferably from 0.1 to 5 microns, more preferably still from 0.1 to 2 microns. Some individual droplets larger than these size ranges may also be present.

The latex may be present when the initial emulsion is formed, in which case the emulsion droplets will begin to combine with the latex immediately they are formed. Alternatively, an emulsion may first be formed by combination of the solution of the pesticide with the emulsifier, in the presence of water, and the emulsion thus formed may thereafter be combined with the latex.

The pesticidal substance employed will generally be one which is non-liquid at 20° C. and preferably one which has a melting point of from 20° to 70° C., since although pesticidal substances with higher melting points than 70° C. and with appreciable solubility in non-aqueous solvents can generally be formulated in this manner, there will often be an alternative formulation type which is more advantageous such as an aqueous suspension concentrate.

In order to form an initial aqueous dispersion of pesticide solution having the desired droplet size, it has been found necessary to employ an emulsifier (i.e. a surfactant). The emulsifier can be incorporated into the continuous (aqueous) phase, (in which case the surfactant preferably has a hydrophile-lipophile balance (HLB) number of 12 or more, usually from 12 to 20). Alternatively the surfactant may be incorporated into the dispersed phase, in which case the surfactant preferably has a HLB number of less than 12.

Surfactants which can be advantageously employed herein can be readily determined by those skilled in the art and include various nonionic, anionic, cationic or amphoteric emulsifiers, or a blend of two or more emulsifiers may be employed. The surfactant employed for the emulsification of the non-aqueous phase should be compatible with the latex and with any surfactants which may be present in the latex composition.

Examples of nonionic surfactants useful in preparing the oil-in-water emulsion include the polyalkylene glycol ethers and condensation products of alkyl phenols, aliphatic alcohols, aliphatic amines or fatty acids with ethylene oxide, propylene oxide or mixtures of ethylene and propylene oxides such as the ethoxylated alkyl phenols or ethoxylated aryl or polyaryl phenols and carboxylic esters solubilized with a polyol or polyoxyethylene. Cationic emulsifiers include quaternary ammonium compounds and fatty amines. Anionic emulsifiers include the oil-soluble (e.g. calcium, ammonium) salts of alkyl aryl sulphonic acids, oil soluble salts of sulphated polyglycol ethers, salts of the esters of sulphosuccinic acid, or half esters thereof with nonionic surfactants and appropriate salts of phosphated polyglycol ethers. Preferred emulsifiers are those which form and stabilize oil-in-water emulsions such as ethoxylated alcohols, alkoxylated alkyl phenols or polyalkylene oxide co-polymers. The surfactant is employed in an amount sufficient to ensure that the emulsion so formed prior to addition of a latex is easily formed and yet does not cause the latex to coagulate. This amount is at least 2% and preferably from 2 to 15%, more preferably from 3 to 10%, and most preferably about 5% by weight of the total composition.

The nature of the water-immiscible solvent for use in the present invention will vary depending upon the pesticidal substance which it is desired to incorporate, and the latex type. Specific examples, however, are the aromatic liquids, particularly alkyl substituted benzenes such as xylene or propyl benzene fractions, and mixed naphthalene and alkyl naphthalene fractions; mineral oils, substituted aromatic organic liquids such as dioctyl phthalate; kerosene, polybutenes; dialkyl amides of various fatty acids, particularly the dimethyl amides of fatty acids such as the dimethyl amide of caprylic acid; chlorinated aliphatic and aromatic hydrocarbons such as 1,1,1-trichloroethane and chlorobenzene, esters of glycol derivatives, such as the acetate of the n-butyl, ethyl, or methyl ether of diethylene glycol, the acetate of the methyl ether of dipropylene glycol, ketones such as isophorone and trimethyl cyclohexanone (dihydroisophorone) and the acetate products such as hexyl, or heptyl acetate. The preferred organic liquids are xylene, propyl benzene fractions, dihydroisophorone, and alkyl acetates.

Pesticidal substances suitable for use in the composition in accordance with the invention include the following insecticides:

| | |
|---|---|
| amitraz | bromophos |
| azinphos-ethyl | bromopropylate |
| azinphos-methyl | butocarboxin |
| *benzoximate | butoxycarboxin |
| bifenthrin | chlordimeform |
| binapacryl | chlorobenzilate |
| bioresmethrin | chloropropylate |
| chlorpyrifos | chlorphoxim |
| chlorpyrifos-methyl | fenamiphos |
| cyanophos | fenobucarb |
| *cyfluthrin | gamma-HCH |
| *cypermethrin | methidathion |
| *deltamethrin | parathion methyl |
| *dicofol | phosalone |
| dioxabenzafos | phosfolan |
| dioxacarb | phosmet |
| *endosulfan | promecarb |
| EPN | quinalphos |
| Ethiofencarb | resmethrin |
| dinobuton | temephos |
| tetradifon | tetramethrin |
| tralomethrin | xylylcarb |
| N-2,3-dihydro-3-methyl-1,3-thiazol-2-ylidene-2,4-xylidine | |
| *1-[3,5-dichloro-4-(1,1,2,2-tetrafluoro ethoxy) phenyl]-3-(2,6-difluorobenzoyl) urea. | | the following fungicides:

| | |
|---|---|
| benalaxyl | myclobutanil |
| bupirimate | nuarimol |
| carboxin | oxycarboxin |
| dodemorph | and ergosterol |
| dodine | biosynthesis inhibitors |
| fenarimol | such as |
| ditalimfos | penconazole |
| | prochloraz |
| | tolclofos-methyl |
| | triadimefon |
| | triadimenol | the following herbicides:

| | |
|---|---|
| aclonifen | chlorpropham |
| alachlor | cycloxydim |
| anilophos | diclofop-methyl |
| benfluralin | diethatyl |
| bensulide | dimethachlor |
| benzoylprop-ethyl | dinitramine |
| bifenox | ethalfluralin |
| bromoxynil | ethofumesate |
| butralin | fenoxaprop ethyl |
| flurochloridone | flamprop-methyl |
| fluchloralin | phenisopham |
| flumetralin | phenmedipham |
| fluorodifen | profluralin |
| fluoroglycofen ethyl | propachlor |
| flurecol butyl | propanil |
| fluoroxypyr ester | pyridate |
| haloxyfop-methyl | *quizalafop-ethyl |
| haloxyfop ethoxyethyl | tridiphane |
| monalide | *trifluralin |
| napropamide | |
| nitrofen | |
| oxadiazon | |
| *oxyfluorfen | |
| *pendimethalin. | |

Of the above active materials, those indicated * have a water solubility of less than 500 ppb, and thus are of direct relevance only to those aspects of the invention concerned with the nature of the polymeric latex.

Other pesticides such as the nitrification inhibitor nitrapyrin may also be employed. The compositions of the invention may also incorporate mixtures of two or more pesticides.

The pesticide may be an organosoluble derivative of a pesticidal compound which is itself poorly organosoluble or insoluble, such as cyhexatin dodecylbenzene sulphonate.

The compositions of the invention may also include optional adjuvants such as freezing point depressants preferably in amounts of 0-15%, flow aids to prevent caking or aid in the redispersion of bottom sediment preferably in amounts of 0-5%, thickening agents preferably amounts of 0-3% and defoamers preferably 0-1% to improve the overall properties under field storage and use conditions.

Similarly conventional pesticide additives such as adjuvant solvents, surfactants for increasing penetration of the active substances or salts may be incorporated into the compositions to maintain or improve biological efficacy of the composition. These may be incorporated into the oil phase or aqueous phase as appropriate.

The compositions of the invention may be prepared by first preparing an oil-in-water emulsion and subsequently adding a polymer latex dispersion, with stirring at a temperature from 0° C. to 100° C., preferably from 10° to 80° C. most preferably from 20° C. to 50° C.

The oil phase may contain from 10 to 80% w/v of the pesticide, preferably 10 to 60% and most preferably 20 to 50% w/v. The latex content of the composition will depend upon the latex type as well as the pesticide and surfactant type but may vary from 5% w/v to 80% w/v, preferably 5 to 60% w/v and most preferably 10 to 50% w/v.

The amount of the latex to be employed in the compositions in the present invention should be as low as possible, provided that it is sufficient to stabilize the emulsion. Not only is the use of excess polymer latex generally uneconomical, it also means that the resulting composition is unable to carry such a high loading of active ingredient, which makes the resulting compositions unattractive to the purchaser.

The latex is preferably used in an amount of less than one part by weight, more preferably less than 0.7 parts by weight, most preferably less than 0.5 parts by weight (calculated as latex solids) per part of the oil phase (i.e. active substance+water immiscible solvent) in the composition.

The emulsion may be prepared prior to addition of the polymer dispersion or by addition of the solution of the pesticide in the non-aqueous solvent to the polymer dispersion. A variety of stirring methods may be employed, from simple shaking, stirring through to sonication and high shear emulsification, including bead milling. The method employed, the temperature chosen and the time taken for equilibration will depend upon a) the nature and amount of the pesticidal compound and solvent employed.

b) the nature and amount of latex employed.

c) the nature and amount of surfactant employed.

The time taken will normally be from one minute to two hours, usually from 5 to 30 minutes, for a laboratory scale process.

The aqueous dispersions in accordance with at least the preferred embodiments of the invention are useful for the control of a wide variety of target organisms, being advantageously employed wherever a conventional emulsifiable concentrate finds use, but having the advantages of being water based and therefore of low flammability, lower dermal toxicity in many cases, ability to be packed in HDPE and being at least as efficacious as an emulsifiable concentrate counterpart. They also have the ability in many cases, since they contain film-forming latexes, to be utilized in those areas where film forming is a desirable effect, such as in seed treatments and pest control in dwelling places.

They are however particularly suitable for an intended for use on growing crops, and to locations in which agricultural crops are to be grown, particulary cereals and the like.

We have also discovered that compositions of the invention show improved long term stability, as compared with the compositions of EP 0080516.

The invention is illustrated by the following Examples.

The following list identifies the various starting materials used in the Examples.

| ACTIVES | | |
|---|---|---|
| | Common Name | Trade Mark |
| A | technical grade chlorpyrifos | DURSBAN-X |
| B | chlorpyrifos-methyl (technical) | RELDAN |
| C | myclobutanil | SYSTHANE |
| D | prochloraz | SPORTAK |
| E | fluoroxypyr 1-methyl heptyl ester | STARANE |
| F | haloxyfop ethoxyethyl | GALLANT |
| G | ditalimfos | PLONDREL |
| H | cyhexatin | PLICTRAN |
| I* | ionoxil octanoacetate | |
| J* | cypermethrin | |
| K | cyfluthrin | |

(*water solubility less than 500 ppb)

| SURFACTANTS | | |
|---|---|---|
| A | ethoxylated alcohol | ATLOX 4991 |
| B | anionic/nonionic blend | BEROL 995 |
| C | anionic/nonionic blend | BEROL 996 |

-continued
SURFACTANTS

| | | |
|---|---|---|
| D | block copolymer | ATLOX G 5000 |
| E | anionic sulphated ether | PERLANKROL PA CONC |
| F | nonionic ethoxylated alcohol | TENSIOFIX PO 132 |
| G | polyaryl phenol ethoxylate | SOPROPHOR BSU |
| J | half ester sulphosuccinate | PESTILISER B |
| I | ethoxylated tallow amine | ETHOMEEN T25 |
| K | anionic/nonionic blend | TENSIOFIX CS |
| L | block copolymer | AGRILAN F502 |

SOLVENTS

| | | |
|---|---|---|
| A | xylene | |
| B | aromatic C9 benzenoid distillate | SOLVESSO 100 |
| C | hexyl acetate | EXXATE 600 |
| D | mixed naphthalene fraction | SOLVESSO 200 |
| E | 1,1,1-trichloroethane | CHLOROTHENE NU |
| F | fatty acid dimethylamide | HALCOMID M-8-10 |
| G | white spirit | |
| H | cyclohexanone | |

POLYMER LATEXES

| | Type | Particle Size (Microns) | Trade Mark | Solids Content |
|---|---|---|---|---|
| A | polystyrene | 1-5 | TEXICOTE 57-0033 | 50% |
| B | terpolymer latex | 0.2-0.3 | VINAMUL 3452 | 50% |
| C | polyvinyl acetate | 0.2-0.8 | VINAMUL 8330 | 63% |
| D | vinyl acetate-ethylene | 0.5-2 | VINAMUL 3254 | 50% |
| E | vinyl acetate-ethylene | 0.2-1 | VINAMUL 3231 | 50% |
| F | vinyl acetete-ethylene | 0.8-1.2 | VINAMUL 3240 | 50% |
| G | acrylic-styrene | 0.5-5.10 | ACRYMUL AMS 161R | 50% |
| H | vinyl acetate-ethylene | 0.5-2 | VINAMUL 3253 | 55% |
| I | acrylic copolymer | 0.5-2.0 | ACRYMUL AMS 160RL | 44% |
| J | polyvinyl acetate | 0.22 | VINAMUL NATIONAL 125-1033 | 55% |
| K | polyvinyl acetate | 2-4 | VINAMUL 8440 | 55% |
| L | polyvinyl acetate | 0.3-0.9 | VINAMUL 9300 | 60% |
| M | polyvinyl acetate | 1-4 | VINAMUL R 98007 | 50% |
| N | vinyl acetate-ethylene | 0.1-0.3 | VINAMUL R 32420 | 50% |
| O | acrylic-styrene | 0.1-1.0 | ACRYMUL AMS 139R | 45% |
| P | acrylic-stryene | 0.1-1.0 | ACRYMUL AMS 377R | 46% |
| Q | acrylic-stryene | 0.1-1.0 | ACRYMUL AMS 179 | 40% |
| R | polyvinyl pyrrolidone | 0.1-1.0 | ANTARA 430 | 40% |
| S | styrene butyl acrylate | 0.12-0.15 | DOW LATEX DL420 | 50% |
| T | styrene butadiene latex | 0.14-0.2 | DOW LATEX DL893 | 47% |
| U | styrene butadiene latex | 0.08-0.15 | DOW LATEX DL277 | 46% |

EXAMPLE 1

Preparation of a chlorpyrifos containing latex 315 g technical grade chlorpyrifos were dissolved in 113 g xylene to produce a 70% w/w chlorpyrifos solution. 428 g of this chlorpyrifos solution were added to 250 g of a polystyrene latex (latex A) containing 50 g of an ethoxylated alcohol surfactant (Surfactant A) and stirred for 30 minutes at ambient temperature.

The product was then diluted to 1 liter with water to produce a composition of which about 43% was constituted by the chlorpyrifos and xylene. No chlorpyrifos or chlorpyrifos solution separated from the mixture on standing for six months. Microscopic examination showed oil phase droplets having a particle size of less than 2 microns against a background of latex particles.

EXAMPLE IA (COMPARATIVE)

428 g of a 70% chlorpyrifos solution in xylene were emulsified into 600 g water containing 50 g Surfactant A and stirred for two hours at ambient temperature. No latex was added. The product was then diluted to 1 liter with water. On standing overnight the oil phase separated, initially as cream but ultimately as an oil phase after about 3 days.

EXAMPLE 2

Preparation of a chlorpyrifos containing terpolymer latex formulation.

315 g technical grade chlorpyrifos were dissolved in 113 g xylene to produce a 70% w/w chlorpyrifos solution. 250 g of a terpolymer latex (Latex B) were added to 150 g water and 50 g Surfactant A to produce a homogeneous dispersion. 428 g of the 70% w/w chlorpyrifos solution were added to the latex/surfactant dispersion with high shear stirring and stirring was continued for 30 minutes. The product was then diluted to 1 liter with water. No chlorpyrifos or chlorpyrifos solution separated on standing. Microscopic evaluation showed very small oil droplets against a background of latex particles with an average particle size of 0.3 microns. This product did not change on storage for six months at 40° C.

EXAMPLE 2A (COMPARATIVE)

Illustrating effect of omission of surfactant on Example 2

315 g technical grade chlorpyrifos were dissolved in 113 g xylene to produce a 70% w/w chlorpyrifos solution. This was added to 250 g of a terpolymer latex (Latex B) under high shear stirring and the stirring continued for two hours. The mixture was then diluted to 1 liter with water and allowed to stand. On standing overnight gross oil separation was apparent, confirmed by microscopic evaluation where very large (more than 300 micron particles) oil droplets were visible, indicating a non-stable product.

EXAMPLES 3–18

In like manner to Example 2 latexes D to R were evaluated according to the base recipe:

| | |
|---|---|
| chlorpyrifos | 315 g tech |
| xylene | 113 g |
| Surfactant A | 50 g |
| latex | 250 g |
| water | balance to 1 liter |

All products were stable formulations with characteristics similar to those of Example 2.

EXAMPLES 19–26

In like manner to Example 2, surfactants B to J were used as alternatives to Surfactant A to prepare compositions according to the base recipe:

| | |
|---|---|
| chlorpyrifos | 315 g tech |
| xylene | 113 g |
| latex B | 250 g |
| surfactant | 50 g |
| water | balance to 1 liter |

| | |
|---|---|
| Example 19 surfactant B | dissolved in oil phase |
| Example 20 surfactant C | dissolved in oil phase |
| Example 21 surfactant D | dissolved in latex |
| Example 22 surfactant E | dissolved in oil phase |
| Example 23 surfactant F | dissolved in latex |
| Example 24 surfactant K | dissolved in oil phase |
| Example 25 surfactant G | dissolved in oil phase |
| Example 26 surfactant J | dissolved in oil phase. |

All products produced were stable formulations with characteristics similar to those of Example 2, the particle size of the emulsion phase varying with the nature of the surfactant.

EXAMPLE 27

Preparation of a latex-containing chlorpyrifos-methyl formulation.

315 g chlorpyrifos methyl (Active B) were dissolved in 184 g xylene to produce a 60% w/w chlorpyrifos methyl solution. 290 g of a terpolymer latex (latex B) were added to 150 g water and 50 g surfactant A to produce a homogeneous dispersion. 499 g of the 60% w/w chlorpyrifos-methyl solution were added to the latex/surfactant dispersion with high shear stirring and stirred for 30 minutes. The product was then diluted to 1 liter with water. No chlorpyrifos methyl or chlorpyrifos-methyl solution separated on standing. Microscopic evaluation showed small oil droplets against a background of latex particles. This product did not change on storage for a period of 6 months.

EXAMPLE 28

Preparation of a latex-containing chlorpyrifos-methyl formulation

The procedure of example 27 was followed, replacing xylene by an aromatic C9-benzenoid distillate (Solvent B). A stable product with similar characteristics to the product of Example 27 was obtained.

EXAMPLE 29

Preparation of a latex-containing myclobutanil formulation

Myclobutanil (60 g) (Active C) was dissolved in Solvent C (180 g) to produce a 25% w/w solution of myclobutanil. 240 g of a terpolymer latex (Latex B) were added to 150 g water and 6 g Surfactant A to produce a homogeneous dispersion. 240 g of the 25% w/w myclobutanil solution were added to the latex/surfactant dispersion with high shear stirring and stirred for 10 minutes. The product was then diluted to 1 liter with water. No myclobutanil or myclobutanil solution separated from the mixture on standing. Microscopic evaluation showed very small oil droplets against a background of latex particles. This product did not change on storage and was suitable as a coating formulation in the treatment of cereal seeds as well as a foliar applied fungicide treatment.

EXAMPLE 30

Preparation of a latex-containing prochloraz formulation

Prochloraz (300 g) was dissolved in Exxate 600 (127 g) to produce a 70% w/w prochloraz solution. 427 g of a terpolymer latex (Vinamul 3452) was added to 50 g water and 4 g Atlox 4991 to produce a homogeneous dispersion. 427 g of the 70% w/w prochloraz solution were added to the latex/surfactant dispersion with high shear stirring and stirred for 20 mintues. The product was then diluted to 1 liter with water. No prochloraz or prochloraz solution separated from the mixture on standing. Microscopic evaluation again showed very small oil droplets against a background of latex particles. The product did not change on storage and was found suitable both as a coating formulation for seed treatment and as a foliar spray for fungicidal treatment of growing crops.

EXAMPLE 31

Preparation of a latex-containing prochloraz/myclobutanil mixed formulation

Prochloraz (120 g) and myclobutanil (60 g) were dissolved in Solvent C (180 g). 360 g of terpolymer latex (Vinamul 3452) was added to 200 g water and 20 g Surfactant A to produce a homogeneous dispersion. 360 g of the prochloraz/myclobutanil solution were added to the latex/ surfactant dispersion with high shear stirring and stirred for 20 minutes. The product was then diluted to 1 liter with water. No prochloraz, myclobutanil or oil solution separated from the mixture on standing. Microscopic evaluation showed very small oil droplets against a background of latex particles, which did not change on storage, indicating an equilibrated stable system.

EXAMPLE 32

Preparation of a latex-containing fluroxypyr 1-methyl heptyl ester formulation

Fluroxypyr 1-methyl heptyl ester (142 g) was dissolved in xylene (150 g) to produce a 48% w/w ester solution. 300 g of a styrene-butylacrylate latex (latex S) was added to 150 g water and 10 g Surfactant I to produce a homogeneous dispersion. 292 g of the ester solution was added to the latex/surfactant dispersion with high shear stirring and stirred for 30 minutes. The product was then diluted to 1 liter with water. No fluroxypyr ester or ester solution separated on standing. Microscopic evaluation showed very small droplets. The product did not change on storage.

COMPARATIVE EXAMPLE 3

575 g of a styrene-butylacrylate latex (latex S) was added to 50 ml water and 80 g Surfactant L. The mixture was heated to 60° C. and molten fluroxypyr 1-methyl heptyl ester (Active E) (302 g) at 60° C. (without a water immiscible solvent) was added to the latex/surfactant dispersion with high shear stirring. The stirring was continued for 1 hour at 60° C. after which time, the mixture was allowed to cool. On standing, the formulation thickened and became unpourable. Microscopic examination showed extensive crystallization throughout the system proving the instability of such a mixture.

EXAMPLE 33

Preparation of a latex-containing fluroxypyr 1-methyl heptyl ester formulation

Fluoroxypyr 1-methyl heptyl ester (Active E) (150 g) was dissolved in Solvent D (150 g) to produce a 50% w/w ester solution. 300 g of a styrene-butylacrylate latex (Latex S) was added to 150 g water and 10 g Surfactant I to produce a homogeneous dispersion. 300 g of the ester solution was added to the latex/surfactant dispersion with high shear stirring and stirring was continued for 30 minutes. The product was then diluted to 1 liter with water. No fluroxypyr ester or ester solution separated on standing. Microscopic evaluation showed very small droplets. The product did not change on storage for 6 months.

EXAMPLES 34-37

In like manner to Example 33, solvents E to H were evaluated according to the base recipe:

| | |
|---|---|
| fluroxypyr 1-methyl heptyl ester | 150 g |
| solvent | 150 g |
| latex S | 300 g |
| Surfactant I | 10 g |
| water | balance to 1 liter |

| | |
|---|---|
| Example 34 | Solvent E |
| Example 35 | Solvent F |
| Example 36 | White Spirit (Solvent G) |
| Example 37 | Cyclohexanone (Solvent H) |

All products were stable formulations with characteristics similar to those of Example 33.

These formulations, when tested on chickweed (*Stellaria media*) and cleavers (*Galium aparine*) using a commercial emulsifiable concentrate as a control were as effective as the commercial concentrate control against the weeds.

EXAMPLE 38

Preparation of a latex-containing fluroxypyr 1-methyl heptyl ester formulation

Fluroxypyr 1-methyl heptyl ester (227 g) was dissolved in Solvent D (182 g) and Solvent F (45 g) to produce a 50% w/w ester solution. 454 g of a styrene-butadiene latex (Latex T) was added to 100 g water and 10 g Surfactant I, to produce a homogeneous dispersion. 454 g of the ester solution was added to the latex/surfactant dispersion with high shear stirring and stirring was continued for 30 minutes. The product was then diluted to 1 liter with water. No fluroxypyr ester or ester solution separated on standing. Microscopic evaluation showed very small droplets. The product did not change on storage for 6 months.

EXAMPLE 39

Haloxyfop ethoxyethyl (Active F) (200 g) was dissolved in xylene (180 g) to produce a 71% w/w ester solution. 380 g of this ester solution was added to a suspension of 480 g styrene-butylacrylate latex (Latex S), and 10 g Surfactant I in water (200 g) at 50° C. with high shear stirring. The stirring was continued for 30 minutes and the product then diluted to 1 liter with water. No haloxyfop ethoxyethyl or ester solution separated on standing. Microscopic evaluation showed very small droplets. The product did not change on storage for 6 months.

EXAMPLE 40

Ditalimfos (Active G) (150 g) was dissolved in xylene (150 g) to produce a 50% w/w solution. 300 g of this solution was added to a suspension of 450 g of a styrene-butadiene latex (Latex U), and 10 g Surfactant I in water (200 g) with high shear stirring. The stirring was continued for 30 minutes and the product then diluted to 1 liter with water. No ditalimfos or ditalimfos solution separated on standing. Microscopic evaluation showed very small droplets. The product did not change on storage for 6 months.

EXAMPLE 41

Technical grade cyhexatin (132 g) was slurried in xylene (238 g) and treated with dodecyl benzene sulphonic acid (106 g). This mixture was stirred with high shear agitation for 10 minutes and then added to a previously prepared latex/surfactant dispersion composed of 500 g terpolymer latex (Latex B) 25 g Surfactant A and water (25 g). The mixture was stirred with high shear for 30 minutes and the product then diluted to 1 liter with water. No cyhexatin, cyhexatin dodecyl benzene sulphate or xylene solution separated on standing. Microscopic evaluation showed very small droplets. The product did not change on storage for 6 months.

EXAMPLE 42

Fluroxypyr 1-methyl heptyl ester (45 g) and ioxynil octanoate (84 g) were dissolved in a mixture of Solvent B and dioctyl phthalate (50 g). To this solution (229 g) was added 10 g of an oil-soluble anionic surfactant (Surfactant J). This oil phase (239 g) was added to a mixture of 230 g of a terpolymer latex (Latex B), and water (30 g) with high shear stirring, and stirring was continued for 30 minutes. The product showed no separation on standing. Microscopic evaluation showed very small droplets. The product did not change on storage for 6 months.

EXAMPLE 43

Surfactant A (50 g) was added to a terpolymer latex (Latex B) (200 g) and water (200 g) and stirred until homogeneous. Cypermethrin (200 g) was mixed with xylene (100 g) and added to this latex/surfactant dispersion with high shear stirring and the stirring continued for 15 minutes. The product was diluted to 1 liter with water to produce a cypermethrin containing latex composition.

EXAMPLE 44

Surfactant A (50 g) was added to a styrene-acrylate latex (Latex Q) (250 g) and water (200 g) and stirred until homogeneous. Cyfluthrin (200 g) was mixed with xylene (100 g) and added to this latex/surfactant dispersion with high shear stirring and the stirring continued for 20 minutes. The product was diluted to 1 liter with water to produce a cyfluthrin containing latex composition.

COMPARATIVE EXAMPLES 1 to 5

The purpose of these comparative examples was to reproduce as closely as possible the examples of GB 2072506.

For reasons of commercial availability, a similar resin (Trade Mark DOW DL 420) was substituted for ACRONYL 290D, and pentachlorophenol was substitued for tetrachlorophenol. The phthlic acid ester used (unspecified in GB 2072506A) was diethylhexylphthalate.

COMPARATIVE EXAMPLE 1

| | | |
|---|---|---|
| Commercially available 50% styrene/ acrylate dispersion (Dow DL 420) | | 40.0% w/w |
| Phthalic acid ester (diethylhexyl phthalate) | (i) | 12.0% w/w |
| Linseed oil | (ii) | 13.0% w/w |
| Pentachlorophenol | (iii) | 18.0% w/w |
| Lindane | (iv) | 4.0% w/w |
| Water | | 13.0% w/w |

Components (i) to (iv) were heated together for four hours at 70° C. to produce a viscous solution. This was added to the latex (DOW DL 420) and water with high shear stirring. The homogeneous product flocculated and oiled in dilution at 1:50 in water.

COMPARATIVE EXAMPLE 2

| | |
|---|---|
| DL 420 | 40.0% w/w |
| Diethylhexylphthalate | 12.0% w/w |
| Linseed oil | 13.0% w/w |
| Chlorpyrifos technical | 22.0% w/w |
| Water | 13.0% w/w |

Chlorpyrifos, diethylhexylphthalate and linseed oil were heated at 40° C. to prepare a clear solution. This was added to the latex/water mixture with high shear stirring. The homogeneous product foculated and oiled on dilution at 1:50 in water.

COMPARATIVE EXAMPLE 3

| | | |
|---|---|---|
| Commercially available homopolymeric polyvinyl acetate dispersion (50%) (TEXICOTE 03-001) | | 42.0% |
| diethylhexylphthalate | (i) | 12.0% |
| Water diluable medium oil alkyd resin | (ii) | 10.0% |
| Pentachlorophenol | (iii) | 20.0% |
| Lindane | (iv) | 3.0% |
| Water | | 13.0% |

Components (i)–(iv) were heated together for four hours at 70° C. to produce a viscous mixture. This was added to the latex and water with high shear stirring. The product was very viscous and did not dilute in water.

COMPARATIVE EXAMPLE 4

| | | |
|---|---|---|
| DL 420 | | 50.0% |
| Lindane | (i) | 6.6% |
| Diethylhexylphthalate | (ii) | 10.0% |
| Linseed oil | (iii) | 10.0% |
| Solvesso 150 (Aromatic hydrocarbon) | (iv) | 9.4% |
| Water | | 14.0% |

Components (i) to (iv) were heated together to form a homogeneous solution. This was then added to the latex/water mixture with high shear stirring. The homogenous product showed oil separating on diluting at 1:50 in water after one hour standing.

COMPARATIVE EXAMPLE 5

| | | |
|---|---|---|
| DL 420 | | 50.0% |
| Chlorpyrifos technical | (i) | 6.6% |
| Diethylhexylphthalate | (ii) | 10.0% |
| Linseed | (iii) | 10.0% |
| Solvesso 150 | (iv) | 9.4% |
| Water | | 14.0% |

Components (i) to (iv) were prepared as in Comparative Example 5 and mixed with latex/water under high shear stirring. The homogeneous product showed oil separation on dilution at 1:50 in water after one hour standing.

We claim:

1. A stabilized aqueous pesticidal concentrate composition for agricultural use which is dilutable with water to at least a dilution of 50:1 by weight, and which has been prepared by forming a solution of a water-immiscible solvent and a pesticidal substance which is not freely soluble in water, has a water solubility of at least 500 parts per billion by weight, and which is soluble in said water-immiscible solvent, combining the said solution with an emulsifier and an aqueous polymer latex suspension containing from about 37 to about 60 percent water, in which the latex is not further polymerizable, to form a dispersion in water of particles comprising said pesticidal substance, wherein the pesticidal substance and the water immiscible solvent together comprise at least 10% by weight of the composition, and wherein the emulsifier is present in an amount sufficient to provide for said dilution of 50:1 by weight.

2. A composition as claimed in claim 1 wherein the pesticide is
chlorpyrifos chlorpyrifos-methyl
tridiphane
haloxyfop ethoxy ethyl
haloxyfop methyl
diclofop-methyl
1-3-(2,6-difluorobenzoyl) urea
myclobutanil
prochloraz
fluroxypyr - 1-methyl heptyl ester
cypermethrin
bromoxynil octanoate
ioxynil octanoate trifluralin.

3. A composition as claimed in claim 1, wherein the composition comprises more than 2% by weight surfactant.

4. A composition as claimed in claim 1, wherein the pesticidal substance has a melting point of from 20° to 70° C.

5. A composition as claimed in claim 1, wherein the amount of the latex employed is such that the weight ratio of latex (calculated as latex solids) to the amount of the said solution of pesticidal substance in water-immiscible solvent is not more than 1:1.

* * * * *